(12) United States Patent
McKay

(10) Patent No.: US 8,257,438 B2
(45) Date of Patent: Sep. 4, 2012

(54) METHODS AND DEVICES FOR PRESERVING MOTION IN AN ARTICULATING PROSTHETIC DISC

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 856 days.

(21) Appl. No.: 11/104,297

(22) Filed: Apr. 12, 2005

(65) Prior Publication Data

US 2006/0229728 A1    Oct. 12, 2006

(51) Int. Cl.
*A61F 2/44*   (2006.01)

(52) U.S. Cl. .................................... 623/17.14; 623/17.15

(58) Field of Classification Search .................. 623/23.6, 623/23.57, 23.36, 23.31, 23.29, 17.14, 17.12, 623/17.15, 20.31, 22.13, 23.39

See application file for complete search history.

(56) References Cited

U.S. PATENT DOCUMENTS

| 1,524,528 | A | | 1/1925 | W.T. Sears |
| 5,068,225 | A | * | 11/1991 | Pennell et al. .................. 514/57 |
| 5,458,643 | A | * | 10/1995 | Oka et al. .................. 623/17.16 |
| 5,662,158 | A | * | 9/1997 | Caldarise ...................... 164/456 |
| 5,866,113 | A | | 2/1999 | Hendriks et al. |
| 5,868,796 | A | * | 2/1999 | Buechel et al. ............ 623/16.11 |
| 5,986,056 | A | | 11/1999 | LaVallie et al. |
| 6,083,930 | A | | 7/2000 | Roufa et al. |
| 6,316,522 | B1 | * | 11/2001 | Loomis et al. ................. 523/105 |
| 6,994,727 | B2 | * | 2/2006 | Khandkar et al. .......... 623/17.15 |
| 2002/0107185 | A1 | | 8/2002 | Spencer |
| 2003/0050689 | A1 | * | 3/2003 | Matson ........................ 623/1.15 |
| 2003/0135277 | A1 | * | 7/2003 | Bryan et al. ................ 623/17.12 |
| 2004/0073310 | A1 | * | 4/2004 | Moumene et al. ......... 623/17.13 |
| 2004/0111159 | A1 | * | 6/2004 | Pope et al. .................. 623/17.14 |
| 2005/0074453 | A1 | | 4/2005 | Ferree |
| 2005/0203627 | A1 | * | 9/2005 | Choksey et al. ........... 623/17.15 |
| 2006/0025862 | A1 | * | 2/2006 | Villiers et al. ............. 623/17.14 |

FOREIGN PATENT DOCUMENTS

| WO | WO 98/08550 | 3/1998 |
| WO | WO 00/74706 A1 | 12/2000 |
| WO | WO 02/30446 A2 | 4/2002 |
| WO | 2005027801 A1 | 3/2005 |
| WO | WO 2005/020955 A1 | 3/2005 |

OTHER PUBLICATIONS

Nakayama et al., "A novel chordin-like BMP inhibitor, CHL2, expressed preferentially in chondrocytes of developing cartilage and osteoarthritic joint cartilage," *Development* 131:229-240 (2004).

Sasai, Y., et al., "*Xenopus chordin*: A Novel Dorsalizing Factor Activated by Organizer-Specific Homeobox Genes," *Cell*, 79:779-790 (1994).

* cited by examiner

*Primary Examiner* — Eduardo C Robert
*Assistant Examiner* — Tara Carter

(57) ABSTRACT

The present invention overcomes the problem of undesirable bone growth and/or unwanted scar tissue formation on the articulating surfaces and in the articulating spaces of prosthetic intervertebral discs. The invention comprises a method for preserving motion in a prosthetic disc having at least one articulating surface comprising applying an anti-infiltration agent on and around an articulating surface of the prosthetic disc. Suitable anti-infiltration agents include but are not limited to, hemostatic compounds, anti-adhesion compounds, bone-formation inhibiting compounds, or any combination thereof.

9 Claims, 2 Drawing Sheets

METHODS AND DEVICES FOR PRESERVING MOTION IN AN ARTICULATING PROSTHETIC DISC

BACKGROUND OF THE INVENTION

Back pain affects millions of people and is a common cause of disability for the middle-aged working population. A frequent cause of back pain is rupture or degeneration of intervertebral discs. Intervertebral discs, located between the endplates of adjacent vertebrae, stabilize the spine, distribute forces between vertebrae, and cushion vertebral bodies. An intervertebral disc includes the annulus fibrosus, a structure that surrounds and confines an inner component, the nucleus pulposus. The annulus fibrosis is composed of a ring of collagen fibers and fibrocartilage embedded in a generally amorphous base substance. The nucleus pulposus is comprised of a mucoid material containing mainly glycoproteins and some collagen. In a healthy, undamaged spine, the annulus fibrosus prevents the nucleus pulposus from protruding outside the disc space and also resists torsional and bending forces applied to the disc.

Intervertebral discs may be displaced or damaged due to disease or aging. Disruption of the annulus fibrosus can allow the nucleus pulposus to protrude into the vertebral canal or intervertebral foramen, a condition known as a herniated or slipped disc. A rupture in the annulus fibrosis can allow the escape of nucleus pulposus components. The extruded nucleus pulposus may press on a spinal nerve, which may result in nerve damage, pain, numbness, muscle weakness and paralysis. Furthermore, as a disc dehydrates and hardens due to age or disease, the disc space height will be reduced, leading to instability of the spine, decreased mobility and pain. Moreover, excessive movement of the spinal segments caused by the disc space height reduction could weaken the annulus fibrosus and, in certain cases, tear it.

Common methods of providing relief for damaged intervertebral discs include surgical removal of all or a portion of the intervertebral disc, followed by fusion of the adjacent vertebrae. Although fusion can eliminate the above symptoms, the restricted motion of the fused segment increases the range of motion required of the adjoining intervertebral discs and could enhance their degeneration.

To overcome the problems with fusion, replacing the entire intervertebral disc with an artificial, articulating disc is believed to be a viable medical alternative to fusion. Many of these articulating invertebral disc devices utilize multicomponent biocompatible polymeric and metallic materials in an attempt to simulate the normal, healthy intervertebral disc motion.

Several obstacles have been addressed in the design and development of prosthetic, articulating intervertebral disc spacers. For example, the disc prosthesis must have immediate and long-term fixation to bone. Immediate fixation may be accomplished with screws, staples, or "teeth" which are integral to the implant. While these techniques may offer long-term stability, other options include porous or macrotexture surfaces which allow for bone in growth.

However, one need that remains unaddressed is the prevention of undesirable bone growth or scar tissue growth on the articulating surfaces or into the articulating spaces of the prosthetic disc implant. Such scar tissue and unwanted bone growth can undermine the effectiveness of the entire replacement disc by inhibiting or preventing the articulation of the prosthetic disc implant in a manner which promotes normal healthy intervertebral disc motion.

SUMMARY OF THE INVENTION

The present invention overcomes the problem of undesirable bone growth and/or unwanted scar tissue formation on the articulating surfaces and in the articulating spaces of prosthetic intervertebral discs. The invention comprises a method for preserving motion in a prosthetic disc having at least one articulating surface comprising applying an anti-infiltration agent to an articulating surface of the prosthetic disc. Suitable anti-infiltration agents include but are not limited to, hemostatic compounds, anti-adhesion compounds, temporary space occupying barrier materials, bone-formation inhibiting compounds, or any combination thereof.

DETAILED DESCRIPTION OF THE INVENTION

Figure 1:
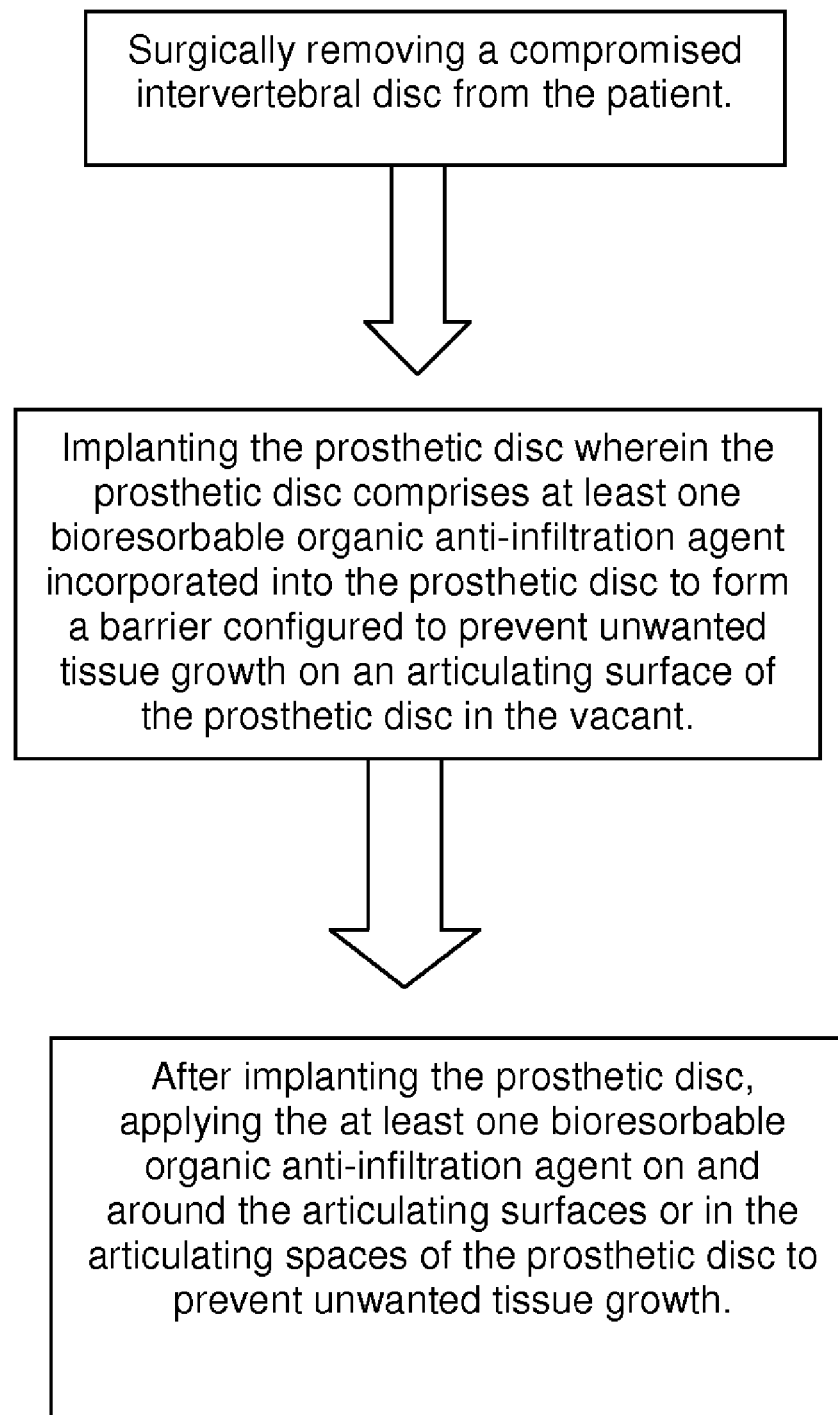
FIG. 1 shows a flow chart with the steps of the method the present invention.
Figure 2:
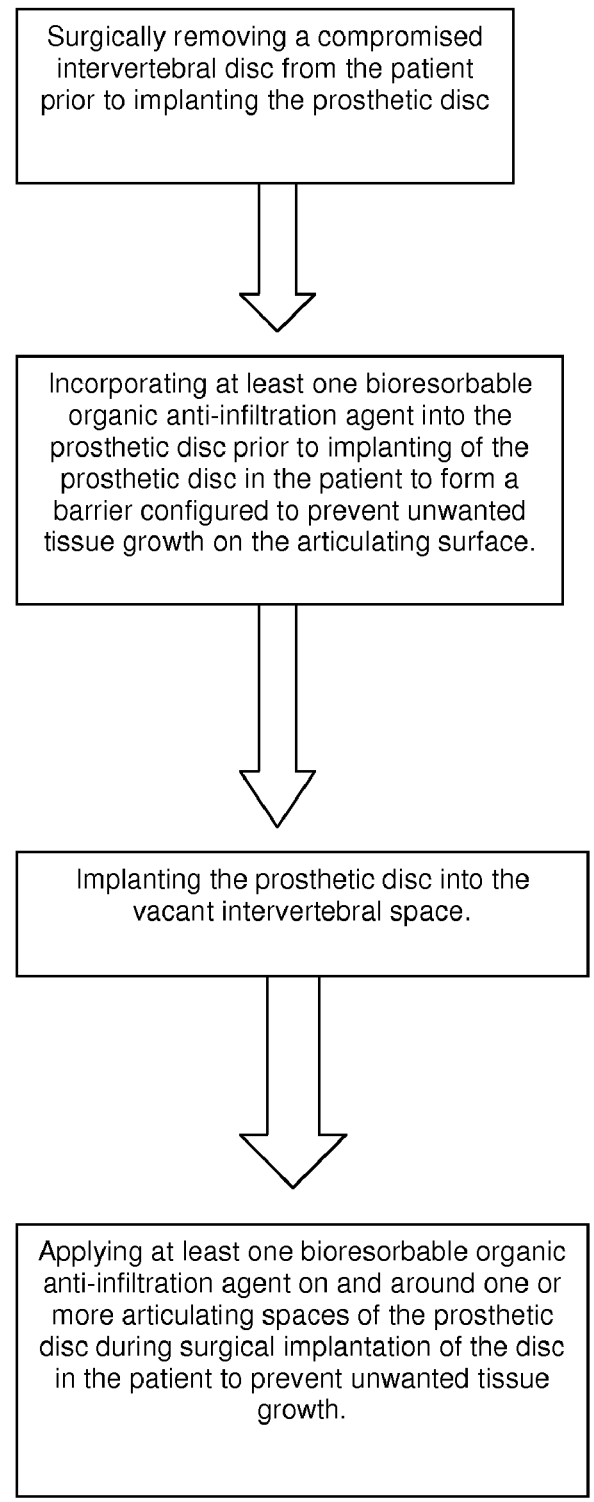
FIG. 2 shows a flow chart of an embodiment of the method shown in FIG. 1.

In accordance with the invention, a method is provided for preserving motion in an articulating prosthetic disc comprising applying a therapeutically effective amount of an anti-infiltration agent to the articulating surfaces of the prosthetic disc. Prosthetic discs having articulating surfaces and spaces are known in the art, and the method of the invention is suitable for any such articulating prosthetic disc. Examples of such articulating prosthetic discs include but are not limited to, SB Charite Artificial Disk (Johnson and Johnson/Dupey/Acromed), Acroflex TDR (Johnson and Johnson/Depuy/Acromed), Spring Disk (Medtronic Sofamer Danek). Maverick (Medtronic Sofamer Danek), ProDisc (Synthes). The invention is particularly suitable for the sizes of the articulating surfaces and the ranges of motion associated with various articulating artificial discs.

Such articulating artificial discs have been reported to become infiltrated with scar tissue or bone formation post surgery, thus reducing or eliminating their motion. During the insertion of the artificial disc, soft tissue and bone are disrupted and bleeding. These disrupted tissues attempt to repair themselves through the release of various growth factors and cells which can migrate into the articulating spaces of the artificial disc. These growth factors and cells can result in the formation of unwanted soft tissue such as adhesions, and unwanted bone growth on the articulating surfaces and into the articulating spaces of the prosthetic disc. Adhesions are abnormal, fibrous bands of scar tissue that can form inside the body following surgery and are triggered by surgical trauma such as cutting, manipulation of suturing, or from inflammation, infection or bleeding. Adhesions generally begin to form within the first several days after surgery. Infiltration by tissues is the body's attempt to fill in empty void spaces.

Preferred anti-infiltration agents used in accordance with the invention include but are not limited to hemostatic agents, anti-adhesion agents, temporary space occupying barrier materials, and bone formation inhibiting compounds, or any combination thereof. Suitable hemostatic agents (agents capable of inhibiting or stopping blood flow) include but are not limited to agents such as Flowseal® (Fusion Medical Technologies, Mountain View, Calif.), Helistat® Integra Life Sciences Products, (Plainsboro, N.J.), Avitene® (Davol, Cranston, R.I.).

Suitable anti-adhesion agents include (agents capable of preventing or inhibiting the formation of post-surgical scar and fibrous bands between traumatized tissues and between traumatized and non-traumatized tissues), but are not limited to, Adcon® (Wright Medical Group, Arlington, Tenn.), Oxiplex® (Fziomed, San Luis Obispo, Calif.), Focal Seal® (Genzyme, Cambridge, Mass.), SprayGel™ adhesion barrier system (Confluent Surgical Inc., San Carlos, Calif.), statins (e.g., lovastatin, simvastatin, pravastatin, fluvastatin, and atorvastatin), anti-VEGF agents (e.g., Avastin™ (Genentech, San Francisco, Calif.), Macugen® (Eyetech Pharmaceuticals, Inc., New York, N.Y.) PCK3145, (Procyon BioPharma, Quebec, Canada), and Anti-TGFβ3 agents (e.g., anti-TGFβ3 antibody, Cyclosporine A (Cs-A) and interferon-γ (IFN-γ).

Suitable bone formation inhibiting compounds include but are not limited to: the bone morphogenic protein (BMP) inhibitor protein known as Noggin, a secreted protein (Nakayama et al., *Development* 131, 229-240 (2004)); Chordin, another secreted protein BMP inhibitor (U.S. Pat. No. 5,986, 056; Sasai, Y., et al., (1994) *Cell* 79, 779-790); Adcon® (Wright Medical Group, Arlington, Tenn.); antisense or RNAi directed against BMP; and high dose TGFβ.

Many of the above materials that are useful as anti-adhesion agents, hemostatic agents, and bone-formation inhibiting compounds are also suitable as temporary space occupying barrier materials including but not limited to Oxiplex® (Fziomed, San Luis Obispo, Calif.). Additional temporary space occupying barrier materials include but are not limited to DuraSeal (Confluent Surgical, Inc., Waltham, Mass.) and other polyethylene glycol materials suitable for use in surgery and with implants. Other suitable temporary space occupying barrier materials include but are not limited to, Flogel® (Alliance Pharmaceuticals), Incert® (Anika Therapeutics), Hylagel® (Genzyme), Interceed® (Ethicon/Johnson & Johnson), Seprafilm® (Genzyme), Gortex® (W.L. Gore), Repel® (Life Medical Sciences), and Quixil® (Omrix Pharmaceuticals).

The present invention includes any formulation of the invention that provides a barrier to the infiltration of unwanted scar tissue or unwanted bone formation on the articulating surfaces and into the articulating spaces of the prosthetic disc. Anti-infiltration agents may be formulated with various excipients and carriers most suitable for the intended method of administering the agent to the articulating surfaces of the prosthetic disc. Anti-infiltration agents of the invention may be formulated as gels, films, solutions, foams sponges and powders with specific characteristics such as adherence, elasticity, strength, viscosity and absorption. A wide variety of biocompatible and pharmaceutically acceptable materials may be used as carriers and excipients. Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic pharmaceutically acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may be used in the preparation of injectables.

Other carriers and components may be used to promote such characteristics such as adherence, elasticity, strength, viscosity and absorption. Preferred formulations of the invention are bioresorbable meaning that the formulation is capable of being resorbed and eliminated from the body after healing is complete. Preferred formulations of the invention may also be bioadhesive and capable of adhering to the living tissue in and around the articulating spaces of the disc in order to form a stable barrier against unwanted scar tissue formation or unwanted bone formation.

In accordance with one embodiment of the invention, a therapeutically effective amount of an anti-infiltration agent is applied on and around the articulating surfaces of the prosthetic disc after the disc is surgically placed in the patient. The anti-infiltration agent may be applied on and around the articulating surfaces by injection, spraying, painting, dripping or by simply pouring the anti-infiltration agent on and around the articulating surface. Preferably, care is taken when applying the anti-infiltration agent not to apply the agent to the non-articulating, surfaces that interface with bone, particularly when osteogenic or osteoinductive compounds are used to promote bone growth at the non-articulating surface to bone interface of the implanted prosthetic disc.

What constitutes a therapeutically effective amount of the anti-infiltration agent will vary depending on factors known to the skilled artisan, such as the specific anti-infiltration agent or combination of agents chosen. In general, the total amount of active agent comprising the anti-infiltration agent is based on volume of substance to fill a particular void space or coat an implant surface. In one embodiment, the total amount of active agent comprising the anti-filtration agent is in the range of about 0.5 to 20 cc's.

In one embodiment, a therapeutically effective amount of an anti-infiltration agent may be coated on the articulating surfaces of the prosthetic disc and/or incorporated into the prosthetic disc, prior to insertion of the disc into the patient during surgery. For example, a solid or liquid carrier containing the infiltration-inhibiting agent may be used to coat the exterior of the prosthetic at its articulating surface (e.g. see U.S. Pat. No. 5,866,113 for examples of coating medical implants). Additionally or optionally, the non-infiltrating agent is incorporated within the device at the articulating surfaces during the manufacture of the prosthetic disc. In one embodiment, the articulating surfaces of the prosthetic disc may be designed to incorporate recesses or textured surfaces to better receive or hold the anti-infiltrating agent. Optionally, additional anti-infiltration agent may be administered separately as discussed above (e.g. by injection, spraying, painting, etc.) during the surgery after the artificial disc that has anti-infiltration agent incorporated into and/or coated onto the articulating surfaces is implanted in the patient.

The invention also provides an articulating prosthetic disc comprising at least one articulating surface and at least one non-articulating surface, wherein an anti-infiltration agent has been incorporated into and/or coated onto the articulating surface of the disc. The non-articulating surface preferably comprises at least one non-articulating, surface-to-bone interface. An osteogenic or osteoinductive agent may optionally be coated on, or incorporated into, the at least one surface-to-bone interface of the non-articulating surface.

The anti-infiltration agent in accordance with any of the above embodiments may further include therapeutically effective amounts of other drugs useful in the methods of the present invention. Such drugs include, but are not limited to: anti-inflammatories, such as aspirin, ibuprofen or other non-steroidal anti-inflammatory drugs; analgesics, or anesthetics, antimicrobial agents, and antibacterial agents.

Surgical methods for implanting prosthetic intervertebral discs are well known. For example, the articulating prosthetic discs described above may be implanted using posterior, lateral and/or anterior approaches. In posterior and some lateral approaches, one or more incisions are made in the back and soft tissues retracted until the targeted portion of the spine is exposed. Intervening anatomy (such as one or more inferior and/or superior facets of the spine) may be removed and/or retracted to allow access to the disk space. In an anterior approach, a small incision is made in the patient's abdomen, below the umbilicus, the abdominal organs are moved to one side, and the disk space is accessed. For all approaches, a discectomy is then performed (if desired) by removing the patient's natural disc. Distraction tools may be used to maintain and/or enhance the spacing between the vertebrae on either side of the removed disc. The prosthetic disc may then be implanted in the space left after removal of the natural disc.

The invention further provides a method for preserving motion in an articulating prosthetic device comprising applying an anti-infiltration agent as described above to the articulating surfaces of the prosthetic device. Prosthetic devices intended for joint repair are particularly suited for this aspect of the invention. Such prosthetic devices include but are not limited to prosthetic hip joints or prosthetic knee joints.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for preserving motion in an articulating prosthetic disc comprising the steps of:
    a) surgically removing a compromised intervertebral disc from the patient prior to implanting the prosthetic disc;
    b) incorporating said at least one bioresorbable organic anti-infiltration agent selected from the group consisting of anti-adhesion agents and bone-formation inhibiting compounds into the prosthetic disc prior to implanting of the prosthetic disc in the patient to form a barrier configured to prevent unwanted tissue growth on said articulating surface;
    c) implanting the prosthetic disc into the vacant intervertebral space; and
    d) applying at least one bioresorbable organic anti-infiltration agent on and around one or more articulating spaces of the prosthetic disc during surgical implantation of the disc in the patient to prevent unwanted tissue growth.

2. The method of claim 1 wherein the anti-infiltration agent is formulated as a gel, film, solution, foam, sponge or powder.

3. The method of claim 1 wherein the application of the anti-infiltration agent to the articulating surfaces does not interfere with desired tissue growth at the non-articulating, implant-to-bone interface surfaces of the prosthetic disc.

4. The method of claim 1 further comprising applying osteogenic or osteoinductive compounds to the non-articulating, implant-to-bone interface surfaces of the prosthetic disc.

5. The method of claim 1 wherein the organic anti-infiltration agent further comprises anti-inflammatory drugs, analgesics, anesthetics, antimicrobial agents, or antibacterial agents.

6. A method for surgically implanting an articulating prosthetic disc in a patient comprising the steps of:
    a) surgically removing a compromised intervertebral disc from the patient;
    b) implanting the prosthetic disc wherein the prosthetic disc comprises at least one bioresorbable organic anti-infiltration agent selected from the group consisting of anti-adhesion agents and bone-formation inhibiting compounds incorporated into the prosthetic disc to form a barrier configured to prevent unwanted tissue growth on an articulating surface of the prosthetic disc in the vacant intervertebral space remaining after removal of the compromised disc; and
    c) after implanting the prosthetic disc, applying the at least one bioresorbable organic anti-infiltration agent on and around the articulating surfaces or in the articulating spaces of the prosthetic disc to prevent unwanted tissue growth.

7. The method of claim 6 wherein the anti-infiltration agent is formulated as a gel, film, solution, foam, sponge or powder.

8. The method of claim 6 wherein the organic anti-infiltration agent further comprises anti-inflammatory drugs, analgesics, anesthetics, antimicrobial agents, or antibacterial agents.

9. The method of claim 6 further comprising the step of applying an osteogenic or osteoinductive agent on and around the non-articulating, implant-to-bone interfaces of the prosthetic disc.

* * * * *